United States Patent [19]

Bradley et al.

[11] Patent Number: 5,196,412
[45] Date of Patent: Mar. 23, 1993

[54] GALLIUM COMPOUNDS

[75] Inventors: Fontaine C. Bradley, Lansdowne; Chris M. Giandomenico, West Chester; Michael J. Abrams, Glenmore; Danielle T. Frost, Philadelphia; Jean F. Vollano, Exton, all of Pa.

[73] Assignee: Johnson Matthey, Inc., Valley Forge, Pa.

[21] Appl. No.: 665,233

[22] Filed: Mar. 6, 1991

[51] Int. Cl.$^5$ ............ A61K 31/555; C07D 223/10; C07D 711/94
[52] U.S. Cl. ............ 514/184; 514/188; 546/6; 556/1; 540/486
[58] Field of Search .......... 546/6; 514/188, 184; 540/486

[56] References Cited

U.S. PATENT DOCUMENTS 4,529,593  7/1985  Warrell et al. ............ 424/127
4,704,277  11/1987  Bockman ............ 424/650

FOREIGN PATENT DOCUMENTS 0271468  6/1988  European Pat. Off.
0325559  7/1989  European Pat. Off.

OTHER PUBLICATIONS

Ivanov, Chem. Abs. 115, 84071 (1991).
Journal of Organometallic Chemistry, vol. 99, No. 2, (1975) pp. 223-230, Schewering et al., "Dialkylmetallhydroxamate . . .".

Primary Examiner—Mark L. Berch
Attorney, Agent, or Firm—Stevens, Davis, Miller & Mosher

[57] ABSTRACT

The present invention relates to compounds of gallium (III) which can be given orally to achieve high serum levels of gallium (III) for the treatment of hypercalcemia of malignancy and related disorders of bone metabolism. Complexes of gallium (III) of the formula (I)

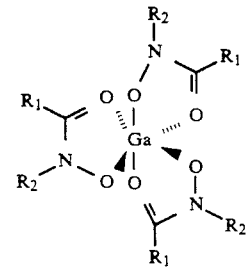

wherein $R_1$ is $C_1$–$C_8$ n-alkyl and $R_2$ is H or $C_1$–$C_2$ alkyl, or $R_1$ and $R_2$ together form tetra- or penta-methylene and wherein said complex is useful in increasing calcium content of bone tissue and decreasing bone resorption, are used in an amount sufficient to cause an increase in calcium content of said bone and to cause decreased bone resorption.

11 Claims, 2 Drawing Sheets

GALLIUM COMPOUNDS

BACKGROUND OF THE INVENTION

Salts of the group III metal gallium have been known for some time to have antitumour activity. More recently, gallium has been shown to reduce serum calcium in patients with hypercalcemia of malignancy. Gallium exerts this latter effect by inhibiting the resorption of calcium from bone; it also increases bone strength so that gallium would also be useful for treating bone disorders associated with accelerated bone loss and decreased bone strength, (see e.g., U.S. Pat. No. 4,704,277 and U.S. Pat. No. 4,529,593).

In practice, gallium therapy for hypercalcemia has been difficult to provide. It has been reported that renal toxicity is dose-limiting when gallium is administered as an i.v. bolus. A seven day continuous i.v. infusion of gallium showed no renal toxicity for the treatment of cancer-associated hypercalcemia, and while this therapy is effective it is cumbersome. In order to make gallium therapy more conveniently administered for both cancer chemotherapy and the hypercalcemia of malignancy, and in order to provide wider application of gallium therapy to appropriate bone diseases, an oral dose form of gallium is highly desirable.

Drug absorption from the gastro-intestinal tract occurs at pH 4.5-7. In this pH range the gallium(III) aquo-ion is extensively hydrolysed to insoluble hydroxides and is very poorly absorbed. Daily oral doses of 400 mg $GaCl_3$ in lung cancer patients yielded mean serum gallium concentrations of $371 \pm 142$ ug/mL. However, gallium in an appropriate co-ordination environment is stable to hydrolysis in aqueous environment, at pH which is relevant biologically.

DESCRIPTION OF THE INVENTION

Figure 1:
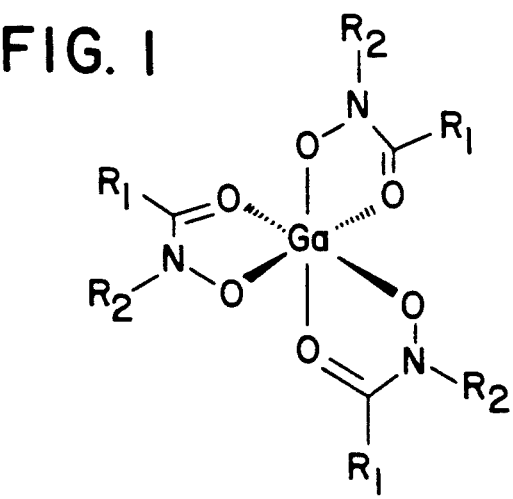
FIG. 1 shows the structural formula of the hydroxamic acid complexes of gallium(III) of the present invention.

The present invention provides novel hydroxamic acid complexes of gallium(III) which produce high serum levels of gallium when given orally, compared to oral gallium salts. These complexes may be represented structurally by Formula I as follows and as shown in FIG. 1.:

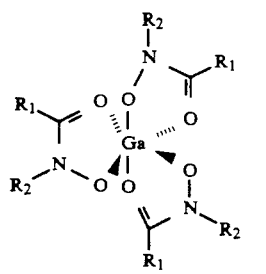

(I)

where $R_1$ is $C_1-C_8$ n-alkyl and $R_2$ or $C_1-C_2$ alkyl, or $R_1$ and $R_2$ together form tetra- or penta-methylene.

(No sterochemistry is implied by this drawing)

These complexes have not been prepared in pharmaceutically acceptable form. The compound of formula I where R is $C_8$ n-alkyl and $R_2$ is $CH_3$ has been disclosed in U.S. Pat. No. 4,741,887 as an extract in the extraction of gallium from aqueous solutions also containing aluminium, iron and zinc.

As representative of the compounds of the invention the following may be mentioned:

| | Preparative Example No. |
|---|---|
| $\left( CH_3(CH_2)_2\overset{O}{\overset{\|}{C}}-\overset{O}{\overset{\|}{N}H} \right)_3 Ga$ | 5 |
| $\left( CH_3(CH_2)_4\overset{O}{\overset{\|}{C}}-\overset{O}{\overset{\|}{N}H} \right)_3 Ga$ | 6 |
| $\left( CH_3(CH_2)_6\overset{O}{\overset{\|}{C}}-\overset{O}{\overset{\|}{N}H} \right)_3 Ga$ | 7 |
| $\left( CH_3\overset{O}{\overset{\|}{C}}-\overset{O}{\overset{\|}{N}CH_3} \right)_3 Ga$ | 1 |
| $\left( CH_3\overset{O}{\overset{\|}{C}}-\overset{O}{\overset{\|}{N}CH_2CH_3} \right)_3 Ga$ | 2 |
| $\left( \begin{array}{c} \overset{O}{\overset{\|}{C}}-\overset{O}{\overset{\|}{N}} \\ (CH_2)_4 \end{array} \right)_3 Ga$ | 3 |
| $\left( \begin{array}{c} \overset{O}{\overset{\|}{C}}-\overset{O}{\overset{\|}{N}} \\ (CH_2)_5 \end{array} \right)_3 Ga$ | 4 |

The complexes of the invention and the necessary starting materials may be prepared by procedures generally known in the art. The gallium-containing starting materials are simple salts of gallium such as $Ga(NO_3)_3$ or $GaCl_3$, or suspensions of freshly precipitated $Ga(OH)_3$. The hydroxamic acids are commercially available or may be prepared by reaction of an appropriate hydroxylamine with a carboxylic acid-ester or chloride to yield the free hydroxamic acid or its salt. (See B. Monzyk et al, J Org Chem, 45, 4680 (1980) and Org Syn Coll Vol II, (1943) John Wiley & Sons, N.Y., p 67).

As noted, the complexes of the invention provide good oral absorption of gallium compared to commercially-available preparations used to treat cancer-related hypercalcemia, when assessed by in vivo tests in rats, as described hereinafter.

The active complexes according to the present inventions may be administered in the form of pharmaceutical compositions formulated according to well known principles. Thus, the composition comprises the active ingredient, preferably in a unit dose, in admixture with a pharmaceutically acceptable diluent or carrier. The active complexes of the invention are assessed to have particular activity when taken orally, and therefore, preferred compositions are those formulated in the form of capsules, tablets, dragees or other solid compositions, or as a solution or suspension, for example as a syrup, for oral administration. Suitable diluents and carriers and other components, and methods for formulation, are generally known.

Although the active complexes of the invention have particular utility for oral administration, the invention is not to be regarded as limited to methods of treatment and compositions solely for oral administration.

Thus, compositions for injections, suppositories, sustained release forms of such or for implantation and the like, may be formulated in conventional manner, and may provide advantages for particular courses of treatment or for combined therapy.

The present invention further provides a method of treatment for excessive loss of calcium from bone in a patient requiring such treatment, comprising administering to the patient an effective dose of an active complex of formula I. Preferably, the administration route is oral.

Dosage rates may suitably lie in the range of 0.1 to 100 mg/kg body weight. Preferably, the dosage is sufficient to maintain a level of 1 to 1.5 μg gallium per ml of blood, and the dose may suitably be in the range 0.5 to 1.5 g of gallium compound per day. Such a dose may be administered as a single unit dose or in a number of smaller unit doses. Other active compounds may be administered separately or together with the gallium complex, or supplemental therapy may be included in a course of treatment for a patient.

EXAMPLE 1

Synthesis of $(CH_3)CON(OH)CH_3$

To 5.27 g $CH_3NHOH.HCl$ in 35 ml MeOH at 0° C. was added with stirring 22 ml $Et_3N$ dropwise. After stirring the suspension for 0.5 hr, 5.78 g $CH_3COCl$ was added dropwise over 5–10 min with vigorous stirring. After allowing the suspension to warm to room temperature, the precipitated $Et_3N.HCl$ was removed by filtration and washed with ether. The ether washings were combined with the filtrate which was then stripped to dryness on a "rotovap" and stirred with 150 ml $Et_2O$ for 10 min. The suspension was filtered and the filtrate stripped to leave 4.3 g yellow oil. The yellow oil was distilled, collecting everything below 90° C. at 50 μm Hg.

Synthesis of $[CH_3CON(O)CH_3]_3Ga$

A chloride-free suspension of freshly precipitated $Ga(OH)_3$ from 20 ml 1.1m aqueous $GaCl_3$ in 120 ml deionised water was stirred with 3.6 g $CH_3CON(OH)CH_3$ for 16 hr. The suspension was centrifuged 10,000 rpm×30 minutes and the supernatant stripped to dryness of the rotovap. The residue was stirred with hot absolute ethanol and the suspension centrifuged 15,000 rpm×40 minutes. The supernatant was decanted and the volume reduced on the "rotovap".

Figure 2A:
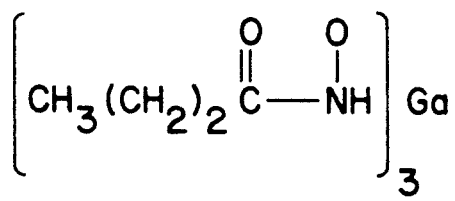
FIGS. 2a-2g show the structural formulae of the gallium complexes of the examples of the present invention.
Figure 2B:
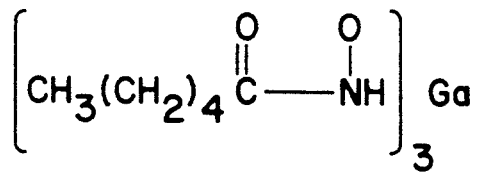
Figure 2C:
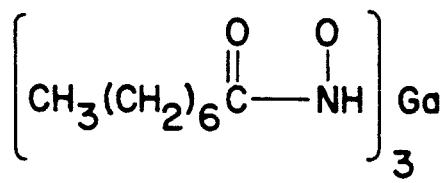
Figure 2D:
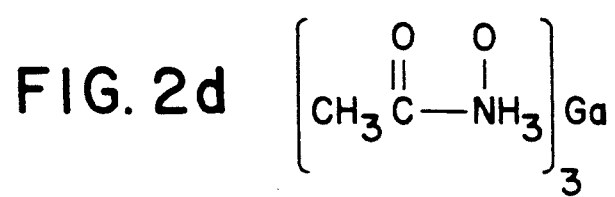

Addition of ether completed precipitation. The solid was filtered, washed with acetone and dried. The structure of this product is shown on page 5 and in FIG. 2d.

Analysis for $C_9H_{18}GaN_3O_6.\tfrac{1}{2}H_2O$

|  | % C | % H | % N | % Ga |
|---|---|---|---|---|
| Calc: | 31.52 | 5.58 | 12.25 | 20.33 |

-continued

|  | % C | % H | % N | % Ga |
|---|---|---|---|---|
| Found | 31.55 | 5.55 | 12.21 | 19.85 |

EXAMPLE 2

Synthesis of $CH_3CON(O)CH_2CH_3$

A mixture of 5 g N-ethylhydroxylamine.HCl and 5.4 g $Na_2CO_3$ was stirred at 0° C. for 1 hour. 4.02 g acetylchloride was added dropwise with stirring maintaining the temperature at 0° C. The suspension was filtered and the filtrate stripped of solvent to leave an oil which was distilled at 1 mm Hg 85° C.

Synthesis of $[CH_3CON(O)CH_2CH_3]_3Ga$

Figure 2E:
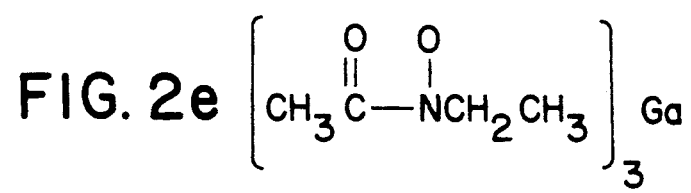

To an aqueous suspension of chloride-free $Ga(OH)_3$ in 40 ml $H_2O$ prepared from 1.6 g $Ga(NO_3)_3.9H_2O$ was added 1.18 g $CH_3CON(OH)CH_2CH_3$. The suspension was stirred overnight, filtered and stripped of solvent to leave an oil. The oil was dissolved in acetone and ether added to precipitate a white solid which was filtered, washed and dried. The structure of this product is shown on page 5 and in FIG. 2e.

Analysis for $C_{12}H_{24}N_3O_6Ga.\tfrac{1}{2}H_2O$

|  | % C | % H | % N |
|---|---|---|---|
| Calc: | 37.43 | 6.54 | 10.91 |
| Found: | 37.48 | 6.46 | 11.14 |

EXAMPLE 3

Synthesis of $Br(CH_2)_4C(O)NH(OCH_2C_6H_5)$

A suspension of 18.75 g of $NH_2OCH_2(C_6H_5).HCl$ in 200 ml $CH_2Cl_2$ was cooled to 0° C. in an ice-NaCl bath. 30.35 ml of triethylamine were added. A solution of 5-bromovavleryl chloride in 70 ml $CH_2Cl_2$ was added dropwise while keeping the temperature of the cold suspension between 0°–5° C. The suspension was stirred cold for 20 minutes, then removed from the bath and stirred at room temperature for 3 hours. The reaction mixture was washed with 3×100 ml 1N HCl, 3×100 ml sat. $NaHCO_3$ and 3×100 ml sat. NaCl solution. The organic layer was dried over $MgSO_4$, filtered and solvent removed to yield 27.38 g of green-grey oil.

Synthesis of $\overline{CH_2CH_2C(O)N(OH)CH_2CH_2}$

To 5 g of $Br(CH_2)_4C(O)NH(OCH_2C_6H_5)$ was added 19.2 of 1M NaOH. The two-phase system was stirred for 30 minutes then extracted with 3×25 ml $CH_2Cl_2$. The organic layers were combined and dried over $MgSO_4$, filtered and solvent removed leaving 3.23 g of white solid. This solid was mixed with 70 ml of 95% EtOH and 0.323 g of 10% Pd on carbon. The mixture was hydrogenated for 1 hour at 50 psi (3.45 bar). The reaction mixture was filtered through diatomaceous earth and the solvent removed leaving 1.70 g of yellowish greasy solid.

Synthesis of $[\overline{CH_2CH_2C(O)N(O)CH_2CH_2}]_3Ga$

Figure 2F:
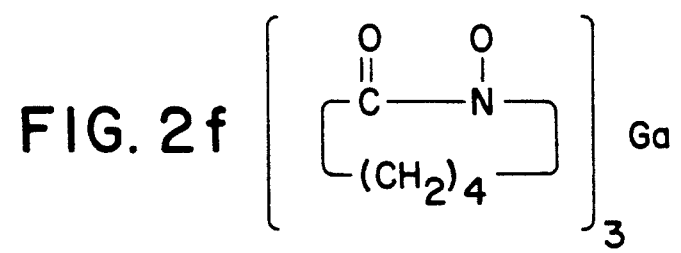

To a suspension of freshly precipitated $Ga(OH)_3$ from 5.9 ml of 1.1M $GaCl_3$ in 40 ml $H_2$) was added a clear solution of 1.5 g $CH_2CH_2CON(OH)CH_2CH_2$ in 60 ml $H_2O$ and stirred for 72 hours at room temperature. The solvent volume was reduced by 25% on the "rotovap"

and centrifuged at 15,000 rpm for 40 minutes. The H$_2$O from the clear supernate was evaporated leaving a gummy residue. The residue was dissolved in 50 ml H$_2$O, filtered through celite and the solvent removed. The remaining yellow lacquer was recrystallised and Abs ethanol/ether to yield 100 mg of orange solid. The structure of this product is shown on page 5 and in FIG. 2f.

Analysis for C$_{15}$H$_{24}$N$_3$O$_6$Ga.½H$_2$O

|  | % C | % H | % N | Ga |
|---|---|---|---|---|
| Calc: | 42.78 | 5.98 | 9.98 | 16.56 |
| Found: | 42.83 | 5.98 | 9.75 | 16.69 |

EXAMPLE 4

Synthesis of BrCH$_2$(CH$_2$)$_4$C(O)NH(OCH$_2$C$_6$H$_5$)

To 4.43 g of NH$_2$OCH$_2$(C$_6$H$_5$).HCl in 50 ml of Ch$_2$Cl$_2$ at 0° C. in an ice-NaCl bath was added 7.17 ml of triethylamine. The temperature was kept between 0°–5° C. while a solution of 3.58 ml 6-bromohexanoyl chloride in 15 ml CH$_2$Cl$_2$ was added dropwise. The mixture was stirred cold for 20 minutes then the ice bath was removed, it was stirred for another 3 hours at room temperature. The mixture was extracted with 3×25 ml 1N HCl solution and 3×25 ml sat. NaCl solution. The organic layer was dried over MgSO$_4$, filtered and stripped of solvent, leaving 6.56 g of oil that solidified after being left open to the air.

Synthesis of $\overline{CH_2CH_2C(O)N(OH)CH_2CH_2CH_2}$

A solution of 18.7 ml of 1M NaOH and 5.1 g of BrCH$_2$(CH$_2$)$_4$CH$_2$NHOCH$_2$-C$_6$H$_5$ were mixed together and heated to 80° C. After 10 minutes, a white precipitate came out of the slightly turbid solution. It was stirred at 80° C. for another 10 minutes. The mixture was extracted with 3×20 ml CH$_2$Cl$_2$. The organic layers were dried over MgSO$_4$, filtered and solvent removed, leaving 3.42 g of yellow oil. The oil was dissolved in 50 ml MeOH, 0.342 g of 10% Pd/C was added and the mixture reduced in a Parr reactor under 50 psi (3.45 bar) H$_2$ for 2 hours. The reaction mixture was filtered through diatomaceous earth, and stripped of solvent leaving 1.91 g of yellow oil which solidified after being exposed to air. The solid was sublimed in a Kugle Rohr apparatus at 50 μm Hg, 60° C. to yield 1.15 g.

Synthesis of $(\overline{CH_2(CH_2)_3C(O)N(O)CH_2})_3$Ga

Figure 2G:
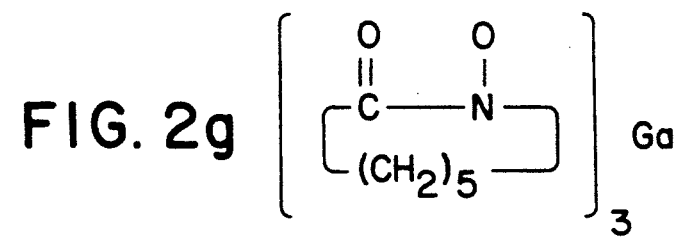

A chloride-free suspension of freshly precipitated Ga(OH)$_3$ from 1.8 ml 1.1M aqueous GaCl$_3$ in 20 ml H$_2$O was stirred with a filtered solution of 0.5 g CH$_2$(CH$_2$)$_3$C(O)N(OH)CH$_2$ in 20 ml of H$_2$O. The suspension was stirred for 3 hours, then heated to 50° C. for 1.5 hours, and finally stirred at room temperature for 15 hours. The cloudy solution was centrifuged at 15,000 rpm for 15 minutes and supernate was stripped of H$_2$O. 450 mg of white solid was collected. The structure of this product is shown on page 5 and in FIG. 2g.

Analysis for C$_{18}$H$_{30}$N$_3$O$_6$Ga

|  | % C | % H | % N | Ga |
|---|---|---|---|---|
| Calc: | 47.60 | 6.66 | 9.25 | 15.35 |
| Found: | 47.36 | 6.68 | 9.13 | 14.62 |

EXAMPLE 5

Synthesis of [CH$_3$(CH$_2$)$_2$CON(O)H]$_3$Ga

To free hydroxylamine in methanol generated from 20 g hydroxylamine hydrochloride and 24.11 g KOH as in Example 6 below was added, 16.47 g ethyl butyrate. The solid KCl which formed was filtered off and washed with methanol. After several hours, more precipitated KCl was filtered off, and the filtrate evaporated of solvent to leave a damp crystalline solid. The solid was recrystallised from hot 8:1 acetone/ethanol, washed with ethyl acetate and dried to yield 8.9 g CH$_3$(CH$_2$)$_2$CON(OK)H.

To 2 g CH$_3$(CH$_2$)$_2$CON(OK)H in 50 ml methanol was added 1.97 g Ga(NO$_3$)$_3$.9H$_2$O in 50 ml methanol. Solid KNO$_3$ was removed by filtration and the filtrate evaporated of solvent. The residue was triturated with 10:1 methylene chloride/methanol to precipitate KNO$_3$ which was removed by filtration. The filtrate was evaporated of solvent to leave a pink oil. The pink oil was stirred in ethyl acetate to yield 1.34 g of white solid. The structure of this product is shown on page 5 and in FIG. 2a.

Analysis for C$_{12}$H$_{24}$N$_3$O$_6$Ga

|  | % C | % H | % N | % Ga |
|---|---|---|---|---|
| Calc: | 38.33 | 6.43 | 11.17 | 18.54 |
| Found: | 38.08 | 6.145 | 11.07 | 18.01 |

EXAMPLE 6

Synthesis of (CH$_3$)(CH$_2$)$_4$CON(O)H]$_3$Ga

Two mixtures of 8.4 g hydroxylamine hydrochloride in 60 ml methanol and 10.2 g KOH in 30 ml methanol were heated to boiling to make complete solutions. To the cooled (40° C.) solution of hydroxylamine hydrochloride, under a N$_2$ flush, was added with stirring the hot methanolic solution of KOH during which a precipitate of KCl formed. After cooling, the mixture was stirred for 5 minutes, and the white solid filtered off. Additional KCl formed in the filtrate and was removed by filtration. The volume of the filtrate was reduced to 100 ml by evaporation and kept at −20° C. for 16 hours. The white gummy crystalline solid which formed was recrystallised from 100 ml hot absolute ethanol. A total of 3 crops yielded 3.7 g CH$_3$(CH$_2$)$_4$CON(OK)H.

To 0.9 ml 1.1M aqueous GaCl$_3$ in 80 ml water at 80° C. was added with stirring 0.5 g (CH$_3$)(CH$_2$)$_4$CON-(OK)H in 10 ml water. The volume of the solution was reduced to 50 ml by evaporation, and a sticky substance formed. The mixture was allowed to stand at room temperature for 16 hours. 40 ml 50/50 methanol/water was added to the mixture which was heated to form a complete solution. 0.25 g white solid was collected after 3 days. The structure of this product is shown on page 5 and in FIG. 2b.

Analysis for C$_{18}$H$_{36}$N$_3$O$_6$Ga/H$_2$O

|  | % C | % H | % N | % Ga |
|---|---|---|---|---|
| Calc: | 45.21 | 8.01 | 8.79 | 14.58 |
| Found: | 45.34 | 7.79 | 8.75 | 14.30 |

EXAMPLE 7

Synthesis of (CH₃)(CH₂)₆CON(O)H)₃Ga

To a stirred suspension of 1 g of CH₃(CH₂)₆CON-(OK)H in 120 ml water was added 2 ml 1.1M aqueous GaCl₃. After about 3 hours the pH was adjusted to 6. A white solid was filtered, washed with water and dried. The white solid was recrystallised by careful addition of water to a methanolic solution of the white solid to yield 550 mg white solid. The structure of this product is shown on page 5 and in FIG. 2c.

Analysis for C₂₄H₄₈N₃O₆Ga.H₂O

|  | % C | % H | % N |
|---|---|---|---|
| Calc: | 51.26 | 8.96 | 7.47 |
| Found: | 51.37 | 8.83 | 7.57 |

According to the invention, compounds were tested for oral absorption in rats. Male Sprague Dawley rats weighing 150-225 g were purchased from Harlan Sprague Dawley, Inc. (Indianapolis, Ind.). The gallium standard solution is from Aldrich Chemical Co (Milwaukee, Wis.). Metofane is a product from Pitman-Moore (Mundelein, Ill.), and all other chemicals are commercially available. Gallium test compounds were dissolved in 18 megaohm water (Millipore, Bedford, Mass.) or suspended in 0.5% carboxymethyl cellulose in 5% ethanol, if the compound was not water soluble. The suspensions were sonicated at room temperature for about 5 minutes.

For stomach and intestine administrations, rats were anaethetised with metofane, and a one-inch incision made to expose the stomach and a portion of the small intestine. A ligation was made immediately below the pylorus, and a second ligation was made one-cm below to assure no leakage. For oral gavage administrations, 18-gauge ball-tipped animal feeding needles (Popper & Sons, Inc, New Hyde Park, N.J.) were used. For stomach injections, needles were inserted in the middle of the pyloric part of the stomach which has an opaque muscular wall, and intestinal injections were made about 0.5 cm below the second ligation with the needle pointed down and away from the stomach.

Sutures were made with 3-4 stitches with 3-0 silk surgical thread (Ethicon Inc, Somerville, N.J.). The tail vein was used for intravenous injections. With the exception of oral gavage administrations, all injections were made with 30-gauge needles to minimise the possibility of leakage. The dose was 0.067 mmol/kg. Approximately 300 μl blood samples were collected at 0.17, 0.5, 1.0, 2.0, 4.0 hours following compound administration. The blood was placed in 1 ml Eppendorf tubes precoated with 50 μl heparin (1,000 U/ml and air dried, so there was no blood dilution involved. The plasma was recovered after the blood was centrifuged for 2 minutes in a Fischer Micro-centrifuge, Model 235B, and its gallium content measured by a Varian Flameless Atomic Absorption Spectrometer. The standard curve was linear in the gallium concentrations of 5-100 ng/ml. The data under the construction versus time curve (AUC) for 0-4 hours was estimated.

Four-Hour Under Curve 0.067 mmol/kg

| Compound | Example No. | 4h-AUC (ng//ml)h |
|---|---|---|
| $\left( \begin{array}{c} O \quad O \\ \| \quad \| \\ [-C-N-] \\ [-(CH_2)_4-] \end{array} \right)_3 Ga$ | 3 | 4469 |
| $\left( \begin{array}{c} O \quad O \\ \| \quad \| \\ CH_3C-NCH_3 \end{array} \right)_3 Ga$ | 1 | 2966 |
| $\left( \begin{array}{c} O \quad O \\ \| \quad \| \\ CH_3(CH_2)_4C-NH \end{array} \right)_3 Ga$ | 6 | 2214 |
| $\left( \begin{array}{c} O \quad O \\ \| \quad \| \\ CH_3(CH_2)_2C-NH \end{array} \right)_3 Ga$ | 5 | 1592 |
| Ga(NO₃)₃ | (Comparison) | 897 |

A solution of gallium nitrate in citrate buffer is given as a control to show the intestinal absorption of a commercial preparation.

The 4-hour AUC's indicate that good oral absorption of gallium occurs from the intestine and that appropriate formulation of the gallium compounds will yield a convenient dose form of gallium for the treatment of cancer, the hypercalcemia of malignancy and other diseases characterised by excessive bone loss and bone weakening.

We claim:

1. A method of administering gallium to a patient, comprising administering an effective dose of gallium-(III) complex of formula I

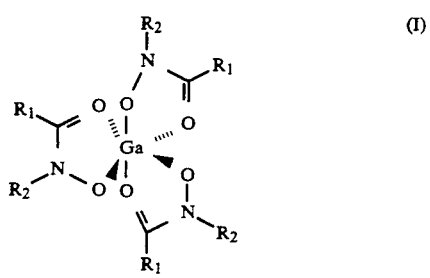

wherein R₁ and R₂ together form tetra- or penta-methylene.

2. A pharmaceutical composition, comprising a pharmaceutically acceptable gallium(III) complex of formula I,

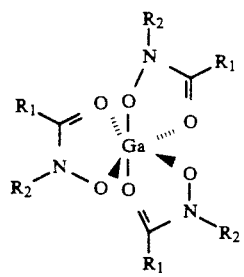

wherein $R_1$ and $R_2$ together form tetra- or penta-methylene, in admixture with a pharmaceutically acceptable diluent or carrier.

3. A gallium(III) complex of formula I,

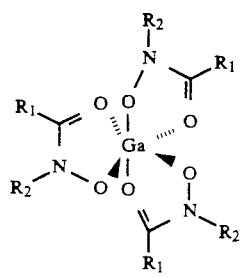

wherein $R_1$ and $R_2$ together form tetra- or penta-methylene.

4. A method of treating excessive loss of calcium from bone tissue and inhibiting bone resorption comprising administering to a patient with an excessive calcium loss and bone resorption disorder, a gallium-(III) complex of formula (I)

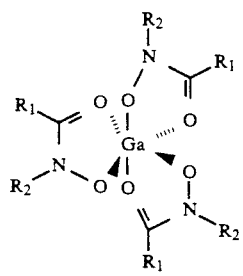

wherein $R_1$ and $R_2$ together form tetra- or pentamethylene;

wherein said complex is useful in reducing calcium loss from bone tissue and inhibiting bone resorption, in an amount sufficient to cause a reduction in calcium loss from said bone and to cause inhibited bone resorption.

5. A composition as claimed in claim 2, in unit dose form for oral administration.

6. The complex of claim 3, which is

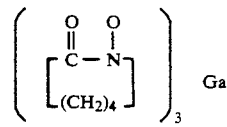

7. The method of claim 1, wherein the complex is

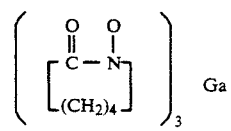

8. The method of claim 1, wherein the complex is

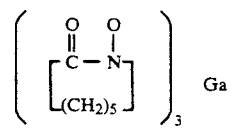

9. The method of claim 1, wherein the route of administration is oral.

10. The method of claim 1, in the treatment of excessive loss of calcium from bone in a patient requiring such treatment.

11. The complex of claim 3, which is

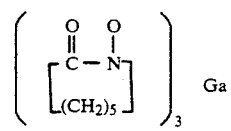

* * * * *